United States Patent
Yokoyama et al.

(10) Patent No.: US 9,233,093 B2
(45) Date of Patent: Jan. 12, 2016

(54) COMPOSITION AND/OR METHOD FOR PREVENTING RECURRENCE OF STROKE

(75) Inventors: Mitsuhiro Yokoyama, Hyogo (JP); Hideki Origasa, Toyama (JP); Masunori Matsuzaki, Yamaguchi (JP); Yuji Matsuzawa, Hyogo (JP); Yasushi Saito, Chiba (JP)

(73) Assignee: MOCHIDA PHARMACEUTICALS CO., LTD., Tokyo (JP)

(*) Notice: Subject to any disclaimer, the term of this patent is extended or adjusted under 35 U.S.C. 154(b) by 573 days.

(21) Appl. No.: 13/558,590

(22) Filed: Jul. 26, 2012

(65) Prior Publication Data

US 2012/0295976 A1 Nov. 22, 2012

Related U.S. Application Data

(63) Continuation of application No. 12/852,558, filed on Aug. 9, 2010, now Pat. No. 8,258,183, which is a continuation of application No. 12/343,974, filed on Dec. 24, 2008, now Pat. No. 7,795,308, which is a continuation of application No. 11/486,091, filed on Jul. 14, 2006, now Pat. No. 7,498,359.

(30) Foreign Application Priority Data

Feb. 7, 2006 (JP) .................................. 2006-29954

(51) Int. Cl.
*A61K 31/22* (2006.01)
*A61K 31/232* (2006.01)

(52) U.S. Cl.
CPC .................................. *A61K 31/232* (2013.01)

(58) Field of Classification Search
USPC .................................................. 514/546, 550
See application file for complete search history.

(56) References Cited

U.S. PATENT DOCUMENTS

| | | | |
|---|---|---|---|
| 6,248,777 | B1 | 6/2001 | Koga et al. |
| 6,673,908 | B1 | 1/2004 | Stanton, Jr. |
| 7,022,713 | B2 | 4/2006 | Aoki et al. |
| 7,498,359 | B2 | 3/2009 | Yokoyama et al. |
| 7,795,308 | B2 | 9/2010 | Yokoyama et al. |
| 2002/0055529 | A1 | 5/2002 | Bisgaier et al. |
| 2003/0060488 | A1 | 3/2003 | Sugiyama et al. |
| 2005/0187292 | A1 | 8/2005 | Aoki et al. |
| 2005/0209329 | A1* | 9/2005 | Horrobin ...................... 514/560 |
| 2006/0111437 | A1 | 5/2006 | Aoki et al. |

FOREIGN PATENT DOCUMENTS

| | | | |
|---|---|---|---|
| GB | 2 388 026 | * | 5/2003 |
| WO | WO-00/48592 A1 | | 8/2000 |
| WO | WO-03/092673 A1 | | 11/2003 |

OTHER PUBLICATIONS

"The GISSI-Prevention Trial Protocol Study of Preventive Measures Relating to the Atherosclerotic and Thrombotic Components of Post-Infarction Risk," G Ital Cardiol, vol. 23, Oct. 1993, pp. 1053-1061, with English translation.
Amarenco et al., "High-Dose Atorvastatin after Stroke or Transient Ischemic Attack," The New England Journal of Medicine, vol. 355, No. 6, Aug. 10, 2006, pp. 549-559.
Canner et al., "Fifteen Year Mortality in Coronary Drug Project Patients: Long-Term Benefit With Niacin," J Am Coll Cardiol, vol. 8, No. 6, Dec. 1986, pp. 1245-1255.
Dyerberg et al., "Hemostatic Function and Platelet Polyunsaturated Fatty Acids in Eskimos," The Lancet, Sep. 1, 1979, pp. 433-435.
Katayama et al., "Effect of Long-Term Administration of Ethyl Eicosapentate (EPA-E) on Local Cerebral Blood Flow and Glucose Utilization in Stroke-Prone Spontaneously Hypertensive Rats (SHRSP)," Brain Research, vol. 761, 1997, pp. 300-305.
Maruyama et al., "Assessment of LDL Particle Size by Triglyceride/HDL-Cholesterol Ratio in Non-diabetic, Healthy Subject Without Prominent Hyperlipidemia," Journal of Atherosclerosis and Thrombosis, vol. 10, No. 3, 2003, pp. 186-191.
Meade et al., "Bezafibrate in Men With Lower Extremity Arterial Disease: Randomised Controlled Trial," BMJ, vol. 25, Nov. 16, 2002, pp. 1-5.
Tsushima, Noh To Junkan (Brain and Circulation), vol. 2, No. 4, pp. 345-349 (1997) with English Translation.
Saeki et al.; Chiryo-gaku (Biomedicine and Therapeutics); vol. 37, No. 9, pp. 995-997 (2003); with English translation.
Katayama et al., Journal of Japanese College of Angiology, vol. 34, No. 8, pp. 477-487 (1994).
Katayama et al.; Progress in Medicine, vol. 21, No. 2, pp. 457-467 (2001) with English Translation.
Fujishima, M.; Igaku no Ayumi (Journal of Clinical and Experimental Medicine); vol. 188, No. 4, pp. 217-222 (1999); with English translation.
Kohriyama, T. et al.; Gendai Iryo (Modern Medicine), vol. 35, No. 1, pp. 533-540 (2003), with English translation.
Drug Interview Form "EPA preparation, Epadel capsule 300", revised in Jul. 2002 and Feb. 2004, Version 21 issued Dec. 2004; pp. 21-22 with English translation of relevant portion only.
Medical Tribune, Issue of Nov. 17, 2005; Special Issue Part 3, pp. 75-76 with English translation.
AHA Scientific Sessions 2005; Circulation vol. 112, No. 21, pp. 3362 (2005).
The Lancet, vol. 354, pp. 447-455 (1999); GISSI—Prevenzione Investigators.
Yzebe et al.; Fundamental Clinical Pharmacology, vol. 18, No. 5, pp. 581-592 (2004).
Kromann, N. et al.; Acta Med Scand. vol. 208, pp. 401-406 (1980).
English translation of certain portion of prosecution history of corresponding Japanese application No. 2006-194043.
Kumar et al., "Protective role of eicosapentaenoate-lipoate (EPA-LA) derivative in combating oxidative hepatocellular injury in hypercholesterolemic atherogenesis," ScienceDirect, Nov. 2006, pp. 115-122.

(Continued)

*Primary Examiner* — Rei-Tsang Shiao
(74) *Attorney, Agent, or Firm* — Birch, Stewart, Kolasch & Birch, LLP

(57) ABSTRACT

By using a composition for preventing onset and/or recurrence of stroke which contains ethyl icosapentate as its effective component, onset and/or recurrence of stroke is prevented, or in particular, the onset and/or recurrence of stroke in a hyperlipidemia patient who has been treated with HMG-CoA RI, or in particular the recurrence of stroke in a patient who is beyond six months after the onset of stroke, is prevented.

18 Claims, 2 Drawing Sheets

(56) References Cited

OTHER PUBLICATIONS

MedicineNet.com, Definition of Stroke [online], retrieved on Jan. 29, 2008, (1999); retrieved from: http://www.medterms.com/script/main/art.asp?articlekey=9791, printed pp. 1-3.

Kurabayashi et al., Eicosapentaenoic Acid Effect on Hyperlipidemia in Menopausal Japanese Women, Obstetrics and Gynecology (2000), 96; 521-528, printed pp. 1-12, especially p. 1.

Yokoyama et al., Effects of eicosapentaenoic acid on cardiovascular events in Japanese patients with hypercholesterolemia; . . . , American Heart Journal, vol. 146, Issue 4 (2003), pp. 613-620, printed pp. 1-14.

Rubins et al., Circulation: Reduction in stroke with Gemfibrozil in Men with Coronary Heart Disease and Low HDL Cholesterol, (2001) 103:2828, printed pp. 1-15, especially pp. 2-4.

Nishimura et al., "The high incidence of left atrial appendage thrombosis in patients on maintenance haemodialysis," Nephrology Dial Transplant, 2003, vol. 18, No. 11, pp. 2339-2347.

Bushnell et al., "Secondary Stroke Prevention Strategies for the Oldest Patients: Possibilities and Challenges," Drugs and Aging, 2009, vol. 26, No. 3, pp. 209-230(22).

\* cited by examiner

COMPOSITION AND/OR METHOD FOR PREVENTING RECURRENCE OF STROKE

CROSS REFERENCE TO RELATED APPLICATIONS

The present application claims the benefit of and is a Continuation of U.S. application Ser. No. 12/852,558, filed Aug. 9, 2010, now U.S. Pat. No. 8,258,183 which is a Continuation of U.S. application Ser. No. 12/343,974, filed Dec. 24, 2008, now U.S. Pat. No. 7,795,308, which is a Continuation of U.S. application Ser. No. 11/486,091, filed Jul. 14, 2006, now U.S. Pat. No. 7,498,359. The benefit of priority is also claimed to Japanese Patent Application No. 2006-29954, filed on Feb. 7, 2006. All of the above are hereby expressly incorporated by reference.

TECHNICAL FIELD

This invention relates to compositions for preventing onset and/or recurrence of stroke which contains at least ethyl icosapentate (hereinafter abbreviated as EPA-E), and methods for administering the composition to a vertebrate including human.

BACKGROUND ART

Stroke is defined as a pathological condition in which impairment of consciousness and neurologic symptom(s) are acutely induced by a cerebrovascular disorder, such as intracerebral hemorrhage and cerebral infarction, and according to a report published by the Ministry of Health, Labor and Welfare, stroke was the third popular cause of death in Japan in 2004. Even if a patient is lucky enough to escape the death, the after effects are often so serious that the quality of life of the patient is greatly impaired. In addition, an onset of stroke is associated with a high risk of its recurrence. Accordingly, stroke has become an issue of public concern.

A relevance of the stroke with hypertension has been known for a long time, and blood pressure control has been advocated and practiced by using various antihypertensives to prevent onset or recurrence of the stroke. As a result, the mortality from stroke of intracerebral hemorrhage type certainly decreased. However, with the westernization of diet and the resulting increase of the patients suffering from so-called "lifestyle-related diseases" such as diabetes, hyperlipidemia and hypertension, the types of stroke in Japan has changed, and today, stroke in Japan consists of about 80% by cerebral infarction, about 15% by intracerebral hemorrhage, and about 5% by subarachnoid hemorrhage. As the cerebral infarction is increasing in accordance with the westernization of diet, attention has brought on the hyperlipidemia among the lifestyle-related diseases, and it has been advocated that arteriosclerotic diseases, namely, myocardial infarction, cerebral infarction, and the like, be prevented by improving cholesterol, especially the low density lipoprotein-cholesterol (LDL-C), also known as "bad cholesterol."

With this as a backdrop, various clinical trials (e.g. KLIS, PATE, J-LIT) using 3-hydroxy-3-methylglutaryl coenzyme A reductase inhibitor (HMG-CoA RI), the so-called "statin agent" having strong hypocholesterolemic action, have been conducted in Japan, and a certain efficacy of statin in preventing onset of cerebral infarction has been suggested. However, for efficacy in secondary prevention of the stroke, namely, prevention of its recurrence, results have not so far been gratifying.

Other exemplary compounds having the action of improving hyperlipidemia are polyunsaturated fatty acids. The polyunsaturated fatty acid is defined as a fatty acid including two or more carbon-carbon double bonds in one molecule, and the polyunsaturated fatty acids are categorized based on the position of the double bond into ω-3 fatty acid, ω-6 fatty acid, and so on. The ω-3 polyunsaturated fatty acids include α-linolenic acid, icosapentaenoic acid (EPA), and docosahexaenoic acid (DHA), and the ω-6 polyunsaturated fatty acids include linoleic acid, γ-linolenic acid, and arachidonic acid. Polyunsaturated fatty acids are derived from natural products, and exhibit various actions including antiarteriosclerotic action, platelet aggregation inhibitory action, hypolipidemic action, anti-inflammatory action, antitumor action, and central action, and with their high degree of safety, they are incorporated in various foods, and sold as health foods or drugs.

It has been reported that the mortality of patients with history of myocardial infarction was decreased by administration of a mixture of ethyl ester of EPA (EPA-E) and ethyl ester of DHA (DHA-E), the ω-3 polyunsaturated fatty acids, for 3.5 years (International Patent Publication No. WO 00/48592). However, this reference does not disclose or suggest whether EPA-E or DHA-E prevents the onset and/or recurrence of stroke.

It has been suggested that administration of a fish oil containing EPA and DHA should prevent brain damage in patients exhibiting atherosclerosis of the artery which feeds blood to the brain (International Patent Publication No. WO 03/92673). However, this reference histologically observed plaques in carotid artery of the patients who have undergone carotid endarterectomy, but fails to demonstrate effects on preventing brain damages and/or the onset of the stroke.

Recently, based on the results of animal experiments and small scale clinical findings, many large scale clinical trials have been planned and performed in order to examine whether various drugs proven to have some effects of improving the lifestyle-related diseases are capable of preventing arteriosclerotic diseases in human. So far, however, the results have not been as expected, and especially the secondary prevention of the stroke is still in a state of trial and error.

High purity EPA-E is commercially available in Japan in the trade names of Epadel and Epadel S (manufactured by Mochida Pharmaceutical Co., Ltd.) as a therapeutic drug for hyperlipidemia. There has been reported that when such high purity EPA-E is orally administered at a dose of 600 mg per administration and 3 times a day immediately after meals (when triglyceride (TG) is abnormal, the dose was increased up to 900 mg per administration and 3 times a day, depending on the degree of the abnormality), the serum total cholesterol (T-Cho) concentration was reduced by 3 to 6%, and the serum TG was reduced by 14 to 20% (Drug Interview Form "EPA preparation, Epadel capsule 300," revised in July, 2002 and February, 2004, version 21 issued in December, 2004; pp. 21-22). It has also been reported in the American College of Cardiology 2005 Annual Meeting that, based on such action, the high purity EPA-E would be expected to have an effect of improving cardiovascular events of hyperlipidemia patients, and its use in combination with statin was effective for inhibiting cardiac events in a large scale clinical trial (Medical Tribune, issue of Nov. 17, 2005, Feature Article Part 3, pp. 75-76; Circulation Vol. 112 (No. 21), pp 3362-3363, 2005). However, these publications do not disclose or suggest that EPA-E prevents onset and/or recurrence of the stroke.

SUMMARY OF THE INVENTION

In view of the situation that the stroke is still a major cause of death and it is a serious problem that many cases of stroke are still impossible to be prevented by the HMG-CoA RI therapy, an object of the present invention is to provide a composition for preventing onset and/or recurrence of the stroke.

In order to solve the problems as described above, the inventors of the present invention made an extensive study and found that EPA-E has an effect of preventing onset and/or recurrence of stroke, and in particular, preventing recurrence of stroke in a patient who is beyond six months after the onset of stroke. The present invention has been completed on the basis of such findings. Accordingly, the present invention includes the following:

(1) A method for preventing recurrence of stroke, including administering ethyl icosapentate orally to a patient with history of stroke at a dose of 0.3 g/day to 6.0 g/day;
(2) A method according to (1), in which the patient is beyond six months after the onset of stroke;
(3) A method according to (2), in which serum TG/HDL-C ratio of the patient is 3.75 or more;
(4) A method according to (3), in which 3-hydroxy-3-methylglutaryl coenzyme A reductase inhibitor is administered to the patient in combination with the ethyl icosapentate;
(5) A method according to (3), in which the administration of the ethyl icosapentate to the patient is continued for at least three years;
(6) A method according to (3), in which a composition having the ethyl icosapentate at a proportion of 96.5% by weight or more in the total content of fatty acids and their derivatives is administered to the patient;
(7) A method according to (2), in which the patient suffers from hyperlipidemia;
(8) A method according to (7), in which 3-hydroxy-3-methylglutaryl coenzyme A reductase inhibitor is administered to the patient in combination with the ethyl icosapentate;
(9) A method according to (7), in which the administration of the ethyl icosapentate to the patient is continued for at least three years; and
(10) A method according to (7), in which a composition having the ethyl icosapentate at a proportion of 96.5% by weight or more in the total content of fatty acids and their derivatives is administered to the patient.

DESCRIPTION OF THE PREFERRED EMBODIMENT

Figure 1:
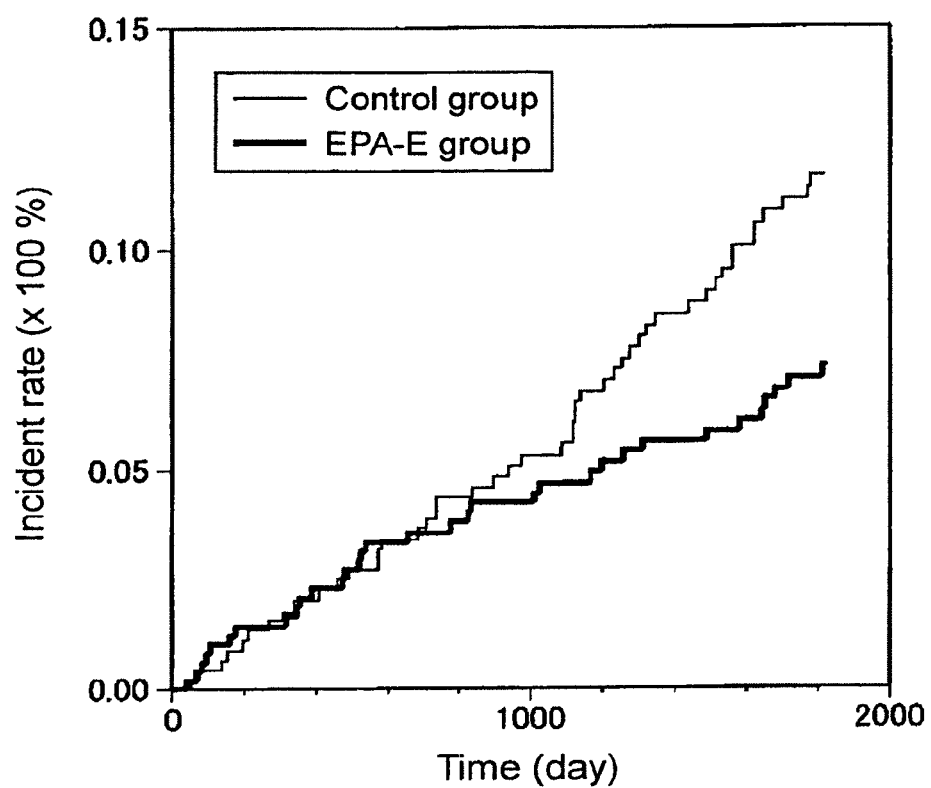
FIG. 1 is a graph prepared by plotting the incidence rate of stroke on Y axis and the time after the start of the trial on X axis, for the EPA-E group and the control group, in an example of the present invention.

Next, the present invention is described in detail.

A first embodiment of the present invention is related to a composition for preventing onset and/or recurrence of stroke, which contains at least EPA-E as its effective component, and a method for administering the composition to a normal individual or a patient with history of stroke. Alternatively, the first embodiment of the present invention is related to a composition for preventing onset and/or recurrence of stroke, which contains at least EPA-E and/or DHA-E as its effective component, and a method for administering the composition to a normal individual or a patient with history of stroke.

The stroke includes all the pathological conditions in which impairment of consciousness and neurologic symptoms is acutely induced by cerebrovascular disorders, and examples include, in particular, intracerebral hemorrhages (hypertensive intracerebral hemorrhage, etc.), cerebral infarction, transient ischemic attack, subarachnoid hemorrhage, cerebral thrombosis (atherothrombotic cerebral infarction, etc.), cerebral embolism (cardiogenic cerebral embolism, etc.), and lacunar infarction. The subjects for the administration include any human who needs prevention of the onset of the stroke, and examples include, in particular, patients of hyperlipidemia.

While the EPA-E content in the total fatty acids of the composition and the dose of the composition are not particularly limited as long as intended effects of the present invention are attained, high purity of EPA-E is preferable, for example, a proportion of the EPA-E in the total fatty acids and their derivatives is preferably 40% by weight or more, more preferably 90% by weight or more, and still more preferably 96.5% by weight or more. The daily dose of the composition in terms of EPA-E is typically 0.3 to 6.0 g/day, preferably 0.9 to 3.6 g/day, and still more preferably 1.8 to 2.7 g/day. Examples of other fatty acids preferably contained in the composition are the ω-3 polyunsaturated fatty acids, in particular, DHA-E. When DHA-E is contained in the composition, while the compositional ratio of EPA-E/DHA-E, the content of EPA-E and DHA-E (hereinafter referred to as (EPA-E+DHA-E)) in the total fatty acids, and the dose of EPA-E+DHA-E, are not particularly limited as long as intended effects of the present invention are attained, the compositional ratio of EPA-E/DHA-E is preferably 0.8 or more, more preferably 1.0 or more, and still more preferably 1.2 or more. High purity of EPA-E and DHA-E is preferable and, for example, the content of EPA-E+DHA-E in the total fatty acids and their derivatives is preferably 40% by weight or more, more preferably 80% by weight or more, and still more preferably 90% by weight or more. The daily dose in terms of EPA-E+DHA-E is typically 0.3 to 10 g/day, preferably 0.5 to 6 g/day, and still more preferably 1 to 4 g/day. The content of other long chain saturated fatty acids is preferably low, and the content of ω-6 fatty acids, and in particular, the content of arachidonic acid, among the long chain unsaturated fatty acids, is preferably as low as less than 2% by weight, and more preferably less than 1% by weight.

A second embodiment of the present invention is related to a composition for preventing onset and/or recurrence of stroke in a hyperlipidemia patient, which contains at least EPA-E, and a method for administering the composition to a hyperlipidemia patient. Alternatively, the second embodiment of the present invention is related to a composition for preventing onset and/or recurrence of stroke in a hyperlipidemia patient, which contains at least EPA-E and/or DIHA-E, and a method for administering the composition to a hyperlipidemia patient.

A third embodiment of the present invention is related to a composition for preventing recurrence of stroke in a patient with history of stroke, which contains at least EPA-E as its effective component, and a method for administering the composition to a patient with history of stroke. Alternatively, the third embodiment of the present invention is related to a composition for preventing recurrence of stroke in a patient with history of stroke, which contains at least EPA-E and/or DHA-E as its effective component, and a method for administering the composition to a patient with history of stroke.

In the second and third embodiments of the present invention, and also in the fourth to thirteenth embodiments of the present invention described later, preferable representatives regarding the type of stroke, the proportion of the EPA-E in the total fatty acids, the proportion of the EPA-E+DHA-E in the total fatty acids, the compositional ratio of EPA-E/DHA-E, the daily dose, and the proportion of the other long chain fatty acids etc., are the same as those in the first embodiment of the present invention as described above.

A fourth embodiment of the present invention is related to a composition for preventing recurrence of stroke in a patient who is beyond six months after the onset of stroke, which contains at least EPA-E as its effective component, and a method for administering the composition to a patient who is beyond six months after the onset of stroke. Alternatively, the fourth embodiment of the present invention is related to a composition for preventing recurrence of stroke in a patient who is beyond six months after the onset of stroke, which contains at least EPA-E and/or DHA-E as its effective component, and a method for administering the composition. In this embodiment, the preferable representatives regarding the type of stroke, the proportion of the EPA-E in the total fatty acids, the proportion of the EPA-E+DHA-E in the total fatty acids, the compositional ratio of EPA-E/DHA-E, the daily dose, and the proportion of the other long chain fatty acids, etc. are the same as those in the first embodiment of the present invention. The subject for the administration is a patient who is beyond six months after the latest onset of stroke and has passed the acute period of the stroke.

A fifth embodiment of the present invention is related to a composition having an excellent effect of preventing recurrence of stroke after 3 years from the start of its administration, which contains at least EPA-E as its effective component, and a method for administering the composition to a patient with history of stroke. In fact, continuous administration of the composition containing at least EPA-E as its effective component to a patient with history of stroke for at least 3 years reduces the incidence rate of the stroke by at least 15% at 3 years from the start of the administration, and by at least 30% at 4 or 5 years from the start of the administration, compared with the control group with no administration of the EPA-E. In particular, when the subject is a patient whose serum TG/HDL-C ratio is 3.75 or more, a continuous administration of the composition containing at least EPA-E as its effective component for at least 3 years reduces the incidence rate of the stroke by at least 20% at 3 years from the start of the administration, and by at least 40% at 4 or 5 years from the start of the administration, compared with the control group with no administration of the EPA-E. Alternatively, the fifth embodiment of the present invention is related to a composition having an excellent effect of preventing recurrence of stroke after 3 years from the start of its administration, which contains at least EPA-E and/or DHA-E as its effective component, and a method for administering the composition to a patient with history of stroke.

A sixth embodiment of the present invention is related to a composition for preventing onset and/or recurrence of stroke, which contains at least EPA-E as its effective component, and is continuously administered to a normal individual or a patient with history of stroke for at least 3 years, in combination with HMG-CoA RI. When the subject is a patient with history of stroke, such combined use reduces the incidence rate of the stroke by at least 15% at 3 years from the start of the administration, and by at least 30% at 4 or 5 years from the start of the administration, compared with the control group with no administration of the EPA-E. In particular, when the subject is a patient whose serum TG/HDL-C ratio is 3.75 or more, a continuous administration of the composition containing at least EPA-E as its effective component in combination with HMG-CoA RI for at least 3 years reduces the incidence rate of the stroke by at least 20% at 3 years from the start of the administration, and by at least 40% at 4 or 5 years from the start of the administration, compared with the control group with no administration of the EPA-E. Alternatively, the sixth embodiment of the present invention is related to a composition for preventing onset and/or recurrence of stroke, which contains at least EPA-E and/or DHA-E as its effective component, and is continuously administered to a normal individual or a patient with history of stroke for at least 3 years, in combination with HMG-CoA RI.

A seventh embodiment of the present invention is related to a method for preventing onset and/or recurrence of stroke, which includes continuously administering a composition containing at least EPA-E as its effective component to a normal individual or a patient with history of stroke for at least 3 years. Alternatively, the seventh embodiment of the present invention is related to a method for preventing onset and/or recurrence of stroke, which includes continuously administering a composition containing at least EPA-E and/or DHA-E as its effective component to a normal individual or a patient with history of stroke for at least 3 years.

A eighth embodiment of the present invention is related to a composition for preventing onset and/or recurrence of stroke which contains at least EPA-E as its effective component, and a method for administering the composition to a subject of a patient whose serum TG/HDL-C ratio is 1 or more, preferably 2 or more, and more preferably 3.75 or more. Alternatively, the eighth embodiment of the present invention is related to a composition for preventing onset and/or recurrence of stroke which contains at least EPA-E and/or DHA-E as its effective component, and a method for administering the composition to a subject of a patient whose serum TG/HDL-C ratio is 1 or more, preferably 2 or more, and more preferably 3.75 or more.

A ninth embodiment of the present invention is related to a composition for preventing recurrence of stroke in a hyperlipidemia patient, which contains at least EPA-E as its effective component, and a method for administering the composition. Alternatively, the ninth embodiment of the present invention is related to a composition for preventing recurrence of stroke in a hyperlipidemia patient, which contains at least EPA-E and/or DHA-E as its effective component, and a method for administering the composition to a hyperlipidemia patient. The preferable representatives regarding the type of stroke, the proportion of the EPA-E in the total fatty acids, the proportion of the EPA-E+DHA-E in the total fatty acids, the compositional ratio of EPA-E/DHA-E, the daily dose, and the proportion of the other long chain fatty acids etc. in the ninth embodiment of the present invention, are the same as those in the first embodiment of the present invention.

A tenth embodiment of the present invention is related to a composition for preventing recurrence of stroke, which contains at least EPA-E as its effective component, and is used in combination with HMG-CoA RI; in other words, a composition to be used in combination with HMG-CoA RI for preventing recurrence of stroke in a patient requiring HMG-CoA RI, which contains at least EPA-E as its effective component, and a method for administering the composition to a patient with history of stroke. Alternatively, the tenth embodiment of the present invention is related to a composition for preventing recurrence of stroke, which contains at least EPA-E and/or DHA-E as its effective component, and is used in combination with HMG-CoA RI; in other words, a composition to be used in combination with HMG-CoA RI for preventing recurrence of stroke in a patient requiring HMG-CoA RI, which contains at least EPA-E and/or DHA-E as its effective component, and a method for administering the composition to a patient with history of stroke.

While the HMG-CoA RI includes everything having inhibitory action on 3-hydroxy-3-methylglutaryl coenzyme A reductase, those pharmaceutically administrable are preferable. An example is preferably selected from the group consisting of pravastatin, simvastatin, lovastatin, fluvastatin, cerivastatin, atorvastatin, pitavastatin, rosuvastatin, and salts and their derivatives, and more preferably, pravastatin, lovastatin, simvastatin, fluvastatin, atorvastatin, pitavastatin, or rosuvastatin, and still more preferably, pravastatin or simvastatin. All pharmaceutically administrable salts are included in the scope of the invention, and preferred are sodium and potassium salts such as pravastatin sodium, fluvastatin sodium, cerivastatin sodium, atorvastatin calcium, pitavastatin calcium, and rosuvastatin calcium. In the present disclosure, all compounds may exist in the form of a salt unless otherwise noted, and "pravastatin," for example, also includes a salt of pravastatin.

An eleventh embodiment of the present invention is related to a composition to be used in combination with HMG-CoA RI for preventing onset and/or recurrence of stroke in a subject of a patient whose serum TG/HDL-C ratio is 3.75 or more, which contains at least EPA-E as its effective component; in other words, a composition to be used in combination with HMG-CoA RI for preventing recurrence of stroke in a patient requiring HMG-CoA RI whose serum TG/HDL-C ratio is 3.75 or more, which contains at least EPA-E as its effective component, and a method for administering the composition to a patient with history of stroke. Alternatively, the eleventh embodiment of the present invention is related to a composition to be used in combination with HMG-CoA RI for preventing onset and/or recurrence of stroke in a subject of a patient whose serum TG/HDL-C ratio is 3.75 or more, which contains at least EPA-E and/or DHA-E as its effective component. In other words, the eleventh embodiment of the present invention is related to a composition to be used in combination with HMG-CoA RI for preventing recurrence of stroke in a patient requiring HMG-CoA RI whose serum TG/HDL-C ratio is 3.75 or more, which contains at least EPA-E and/or DHA-E as its effective component, and a method for administering the composition to a patient with history of stroke. Patients requiring HMG-CoA RI suffer from hyperlipidemia in many cases.

The compositions and the methods in the seventh to eleventh embodiments of the present invention are preferably compositions and methods for a patient with history of stroke, and more preferably compositions and methods for a patient beyond six months after the onset of stroke, i.e., a patient who has passed the acute period of stroke.

A twelfth embodiment of the present invention is related to a method for preventing onset and/or recurrence of stroke in a patient whose serum TG/HDL-C ratio is 3.75 or more, which includes administering a composition containing at least EPA-E as its effective component to the patient, until the TG/HDL-C ratio becomes less than 3.75, more preferably less than 1. Alternatively, the twelfth embodiment of the present invention is related to a method for preventing onset and/or recurrence of stroke in a patient whose serum TG/HDL-C ratio is 3.75 or more, which includes administering a composition containing at least EPA-E and/or DHA-E as its effective component to the patient, until the TG/HDL-C ratio becomes less than 3.75, more preferably less than 1.

A thirteenth embodiment of the present invention is related to use of EPA-E in manufacture of a composition for preventing onset and/or recurrence of stroke. Alternatively, the thirteenth embodiment of the present invention is related to use of EPA-E and/or DHA-E in manufacture of a composition for preventing onset and/or recurrence of stroke.

While the EPA-E content in the total fatty acids of the composition and the dose of the composition are not particularly limited as long as intended effects of the present invention are attained, high purity of EPA-E is preferable and, for example, a proportion of the EPA-E in the total fatty acids and their derivatives of the composition is preferably 40% by weight or more, more preferably 90% by weight or more, and still more preferably 96.5% by weight or more. The daily dose of the composition in terms of EPA-E is typically 0.3 to 6 g/day, preferably 0.9 to 3.6 g/day, and still more preferably 1.8 to 2.7 g/day. Examples of other fatty acids preferably contained in the composition are the ω-3 polyunsaturated fatty acids, in particular, DHA-E. When DHA-E is contained in the composition, while the compositional ratio of EPA-E/DHA-E, the content of EPA-E+DHA-E in the total fatty acids, and the dose of EPA-E+DHA-E are not particularly limited as long as intended effects of the present invention are attained, the compositional ratio of EPA-E/DHA-E is preferably 0.8 or more, more preferably 1.0 or more, and still more preferably 1.2 or more. High purity of EPA-E and DHA-E is preferable and, for example, the content of the EPA-E+DHA-E in the total fatty acids and their derivatives is preferably 40% by weight or more, more preferably 80% by weight or more, and still more preferably 90% by weight or more. The daily dose of the composition containing DHA-E in terms of EPA-E+DHA-E is typically 0.3 to 10 g/day, preferably 0.5 to 6 g/day, and still more preferably 1 to 4 g/day. The content of other long chain saturated fatty acids is preferably low, and the content of ω-6 fatty acids, and in particular, the content of arachidonic acid, among the long chain unsaturated fatty acids, is preferably as low as less than 2% by weight, and more preferably less than 1% by weight.

The composition of the present invention contains EPA-E and/or DHA-E and has the effect of preventing onset and/or recurrence of stroke when orally administered to a normal individual or a patient having the risk factor for stroke such as hyperlipidemia, diabetes, and hypertension. In particular, the composition of the present invention has the effect of preventing onset and/or recurrence of stroke in a hyperlipidemia a patient who has been treated with HMG-CoA RI. The composition of the present invention also has a combined effect when used in combination with HMG-CoA RI, and accordingly, onset and/or recurrence of stroke can be even more effectively prevented by the combined use.

The composition of the present invention may be appropriately used in combination with at least a drug commonly used for preventing onset and/or recurrence of stroke, which is, for example, selected from the group including antiplatelets such as aspirin, ticlopidine, clopidogrel, and cilostazol; anticoagulants such as warfarin, heparin, and ximelagatran; antihypertensives such as angiotensin II receptor antagonists (candesartan, losartan, etc.), angiotensin converting enzyme inhibitors, calcium channel antagonists (amlodipine, cilnidipine, etc.), and α-1 blockers; drugs for diabetes or for improving abnormal glucose tolerance such as α-glucosidase inhibitors (voglibose, acarbose, etc.), biguanides, thiazolidinediones (pioglitazone, rosiglitazone, rivoglitazone, etc.), and fast-acting insulin secretagogues (mitiglinide, nateglinide, etc.); and antihyperlipidemics such as the HMG-CoA RI described above, fibrates, squalene synthase inhibitors (TAK-475, etc.), and cholesterol absorption inhibitors (ezetimibe, etc.). It is noted that the composition of the present invention can be used in a package together with at least one drug such as HMG-CoA RI and/or others for improving convenience.

The composition of the present invention contains less impurities such as saturated fatty acids and arachidonic acid which are unfavorable for stroke compared to fish oil or fish oil concentrate, and its intended effects can be attained without causing problems such as overnutrition and excessive intake of vitamin A. In addition, since the effective component of the present composition is an ester and thus more stable against oxidation compared to the fish oil etc. which are essentially in the form of triglyceride, a sufficiently stable composition can be produced by adding a conventional antioxidant. Therefore, the use of the EPA-E has enabled production of a composition for preventing onset and/or recurrence of stroke which can be used in clinical practice, for the first time.

In the present specification, the term "icosapentate" designates all-cis-5,8,11,14,17-icosapentaenoic acid.

In the present specification, the term "stroke" is defined as a pathological condition in which impairment of consciousness and neurologic symptom(s) are acutely induced by a cerebrovascular disorder, which includes intracerebral hemorrhages (hypertensive intracerebral hemorrhage, etc.), cerebral infarction, transient ischemic attack, subarachnoid hemorrhage, cerebral thrombosis (atherothrombotic cerebral infarction, etc.), cerebral embolism (cardiogenic cerebral embolism, etc.), and lacunar infarction.

In the present specification, the term "hyperlipidemia patient" designates a patient experiencing either an increase in serum T-Cho concentration, an increase in serum LDL-Cho concentration, a decrease in serum HDL-Cho concentration, or an increase in serum TG. In a narrow sense, the term "hyperlipidemia patient" designates a patient who suffers from any one of hypercholesterolemia (with the serum T-Cho concentration of about 220 mg/dl or higher, and in a narrower sense, 250 mg/dl or higher), hyper-LDL cholesterolemia (with the serum LDL-Cho concentration of 140 mg/dl or higher), hypo-HDL cholesterolemia (with the serum HDL-Cho concentration of less than 40 mg/dl) and hypertriglyceridemia (with the serum TG of 150 mg/dl or higher). Serum concentration of each lipid can be measured and calculated by conventional methods, typically using blood samples collected during fasting. The serum TG/HDL-C ratio is a value obtained by dividing the serum concentration of triglyceride (TG) by the serum concentration of high density lipoprotein-cholesterol (HDL-C).

TG/HDL-C ratio is known to have an inverse correlation with particle diameter of LDL according to a report for subjects of normal individuals by Maruyama et al. (J. Atheroscler. Thromb., Vol. 10, pp. 186-191, 2003), in which the correlation was so found as the LDL particle diameter is 25.5 nm when TG/HDL-C ratio is 1. Among LDLs, small dense LDL (sdLDL) with the particle diameter of 25.5 nm or less, also known as "super-bad cholesterol" has a strong effect to induce arteriosclerosis, and thus the TG/HDL-C ratio has recently drawn attentions as one of the criteria for the prognosis of arteriosclerotic diseases. According to the correlation mentioned above, the sdLDL starts to appear when the TG/HDL-C ratio becomes 1 or more, whereby increasing the risk for arteriosclerotic diseases. Thus the cut-off value for the serum TG/HDL-C ratio is set to 3.75 in the present invention based on the reference value of 150 mg/dl for the TG and the reference value of 40 mg/dl for HDL-C. Patients whose serum TG/HDL-C ratio are 3.75 or more have high serum sdLDL concentration, and are predicted to have a high risk for onset of stroke. Both the high TG value and the low HDL-C are considered as the risk factors for the arteriosclerotic diseases.

However, when the TG is 400 mg/dl or more, chylomicronemia would be suspected, but chylomicronemia is considered not to be arteriosclerotic. In view of this, when the results were analyzed based on the TG/HDL-C ratio in the embodiment of the present invention, those cases where the serum TG value at the time of registration was 400 mg/dL or more were excluded from the subjects for the analysis.

In the present specification, the term "use of EPA-E in combination with HMG-CoA RI" includes both the embodiment in which the EPA-E and the HMG-CoA RI are simultaneously administered and the embodiment in which both agents are separately administered. When they are simultaneously administered, they may be formulated either as a single combination drug, or separate drugs. When they are separately administered, EPA-E may be administered either before or after HMG-CoA RI. The dose and ratio of EPA-E and HMG-CoA RI may be adequately selected.

In the present specification, the term "use of EPA-E and/or DHA-E in combination with HMG-CoA RI" include both the embodiment in which the EPA-E and/or DHA-E and the HMG-CoA RI are simultaneously administered and the embodiment in which both agents are separately administered. When they are simultaneously administered, they may be formulated either as a single combined drug, or separate drugs. When they are separately administered, EPA-E and/or DHA-E may be administered either before or after the HMG-CoA RI. The dose and ratio of EPA-E and/or DHA-E and HMG-CoA RI may be adequately selected.

The composition of the present invention has the action of preventing onset and/or recurrence of the stroke by sole administration of the composition, and in particular, the composition is expected to have the effect of preventing onset and/or recurrence of stroke which cannot be prevented by sole administration of HMG-CoA RI. In addition, EPA-E has not only the action of reducing the serum T-Cho concentration and the serum TG, but also the pharmacological actions such as suppressing platelet aggregation based on inhibition of arachidonic acid cascade, which are different from those of HMG-CoA RI. Therefore, the action as described above can also be exerted by combined administration with HMG-CoA RI.

Since EPA-E and DHA-E are highly unsaturated, inclusion of an effective amount of an antioxidant, such as butylated hydroxytoluene, butylated hydroxyanisole, propyl gallate, gallic acid, and pharmaceutically acceptable quinone, and a-tocopherol, is preferable.

The preparation may be orally administered to a patient in a dosage form such as tablet, capsule, microcapsule, granules, fine granules, powder, oral liquid preparation, syrup, and jelly. Preferably, the preparation is orally administered by filling in a capsule such as soft capsule or microcapsule.

It is noted that the soft capsule containing high purity EPA-E (Epadel and Epadel S) are commercially available in Japan as safe therapeutic agents for arteriosclerosis obliterans and hyperlipidemia with reduced side effects, and in these products, the proportion of the EPA-E in the total fatty acids is at least 96.5% by weight. Soft capsule (Omacor, Ross products) containing about 46% by weight of EPA-E and about 38% by weight of DHA-E is commercially available in the U.S and other countries as a therapeutic agent for hypertriglyceridemia. These commercial drugs may be obtained for use in the present invention.

The dose and the period of administration of the composition for preventing onset and/or recurrence of stroke according to the present invention should be sufficient for the expression of the intended action, and may be adequately adjusted depending on, for example, the dosage form, administration route, number of doses per day, severity of the symptom, body weight, age, and the like. When orally administered, the composition may be administered at a dose in terms of EPA-E of 0.3 to 6 g/day, preferably 0.9 to 3.6 g/day, and more preferably 1.8 to 2.7 g/day, and while the composition is typically administered in 3 divided doses a day, if necessary, the composition may be administered in a single dose or in several divided doses. The composition is preferably administered during or after the meal, and more preferably, immediately (within 30 minutes) after the meal. When the composition is orally administered, the administration period is typically at least 1 year, preferably at least 2 years, more preferably at least 3 years, and most preferably at least 5 years. The administration is preferably continued as long as there is a high risk of onset and/or recurrence of stroke. If desired, drug holidays of about 1 day to 3 months, preferably about 1 week to 1 month, may be given.

The HMG-CoA RI to be used in combination is preferably administered according to the recommended dosage regimen, and the dose may be adequately adjusted depending on, for example, its type, dosage form, administration route, number of doses per day, severity of the symptoms, body weight, sex, age, and the like. When orally administered, the HMG-CoA RI is typically administered at a dose of 0.05 to 200 mg/day, and preferably 0.1 to 100 mg/day in 2 to 3 divided doses a day, but if desired, it may be administered in a single dose or in several divided doses. The dose of the HMG-CoA RI may be reduced depending on the dose of the EPA-E.

It is noted that pravastatin sodium (Mevalotin™ tablets and fine granules, Sankyo Co., Ltd.), simvastatin (Lipovas™ tablets, Banyu Pharmaceutical Co., Ltd.), fluvastatin sodium (Lochol™ tablets, Novartis Pharma K.K. and Tanabe Seiyaku Co., Ltd.), atorvastatin calcium hydrate (Lipitor™ tablets, Astellas Pharma Inc. and Pfizer), pitavastatin calcium (Livalo™ tablets, Kowa Company, Ltd. and Sankyo Co., Ltd.), and rosuvastatin calcium (Crestor™ tablets, AstraZeneca K.K. and Shionogi & Co., Ltd.) are commercially available in Japan as antihyperlipidemics, and lovastatin (Mevacor™ tablets, Merck) is commercially available in the U.S. as a antihyperlipidemic. At least one of these commercial drugs may be obtained and appropriately combined for administration according to the directions recommended for them.

The preferable daily doses of these drugs are, for example, 5-60 mg or preferably 10-20 mg for pravastatin sodium, 2.5-60 mg or preferably 5-20 mg for simvastatin, 10-180 mg or preferably 20-60 mg for fluvastatin sodium, 5-120 mg or preferably 10-40 mg for atorvastatin calcium hydrate, 0.5-12 mg or preferably 1-4 mg for pitavastatin calcium, 1.25-60 mg or preferably 2.5-20 mg for rosuvastatin calcium, 5-160 mg or preferably 10-80 mg for lovastatin, and 0.075-0.9 mg or preferably 0.15-0.3 mg for cerivastatin, but not limited to them.

EXAMPLES

Next, the effects of the composition according to the present invention are demonstrated by referring to Examples, which by no means limit the scope of the present invention.

Example 1

Long Term Preventive Action of EPA-E on the Onset of Stroke

Trial Procedure

This trial is a partial analysis of the results obtained in DELIS (Japan EPA Lipid Intervention Study), a large scale clinical trial of high purity EPA preparation which was presented at the American College of Cardiology 2005 Annual Meeting. It should be noted that while an inhibitory effect of EPA on coronary events was reported in the Meeting, there was no disclosure or suggestion of its effect on stroke (for general information on DELIS, see Medical Tribune, issue of Nov. 17, 2005, Feature Article Part 3, pp. 75-76, and Circulation vol. 112 (No. 21), pp. 3362-3363, 2005; which are incorporated herein by reference).

Specifically, of the 18,645 subject patients in the DELIS trial (hyperlipidemia patients with serum T-Cho concentration of 250 mg/dl or more, at ages of 40 to 75 for male and postmenstrual to 75 for female; the patients within six months from the onset of stroke were excluded in order to exclude patients in the acute period of the stroke from the trial subjects) (EPA-E group (9,326 cases) and control group (9,319 cases)), 485 subjects from the EPA-E group and 457 subjects from the control group, having history of stroke (cerebral thrombosis, cerebral embolism, intracerebral hemorrhage, subarachnoid hemorrhage, and transient ischemic attack) were observed and analyzed for the recurrence of stroke during the period of 5 years from the start of the administration. Further, for the cases where serum TG/HDL-C ratio was known (but excluding the cases where TG value was 400 mg/dl or more), results from the subjects divided into three groups based on the serum TG/HDL-C ratio at the time of registration were also analyzed. The EPA-E group was orally administered with Epadel (Mochida Pharmaceutical Co., Ltd.) typically at an adult dose of 600 mg per administration and 3 times a day immediately after the meal. However, in the cases having abnormal serum TG, the dose could be increased up to 900 mg per administration and 3 times a day, depending on the abnormality. In both groups, pravastatin sodium (Mevalotin™ tablets and fine granules, Sankyo Co., Ltd.), simvastatin (Lipovas™ tablets, Banyu Pharmaceutical Co., Ltd.), or atorvastatin calcium hydrate (Lipitor™ tablets, Astellas Pharma Inc. and Pfizer) was used as a base drug (basal treatment), which was orally administered according to a predetermined dosage regimen.

Results

The number of onset (recurrence) of stroke, the incidence rate (%), and the odds ratio for the EPA-E group in relation to the control group during the observation period of 5 years are shown in Table 1. The odds ratio was calculated by the equation of (incidence rate of the EPA-E group)/(incidence rate of the control group), and the inhibition rate of onset of stroke was calculated by the equation of {((incidence rate of stroke for the control group)−(incidence rate of stroke for the EPA-E group))/(incidence rate of stroke for the control group)}×100.

TABLE 1

| Control group<br>Stroke cases/All cases<br>(incidence rate, %) | EPA-E group<br>Stroke cases/All cases<br>(incidence rate, %) | Odds ratio |
|---|---|---|
| 48/457<br>(10.5) | 33/485<br>(6.8) | 0.648 |

As a result of the EPA-E administration, the incidence rate of the stroke over 5 years in the patients who had the history of the stroke was reduced to 6.8% compared with the incidence rate of the stroke in the control group of 10.5%. The odds ratio was 0.648, and the incidence rate of the stroke was reduced by about 35% compared with the control group by the administration of EPA-E. Accordingly, the effect of EPA-E administration on preventing onset of stroke in patients with history of stroke was shown.

Further, the data described above were statistically analyzed by taking biases in the background (smoking habit, diabetes, etc.) between the groups into consideration. FIG. 1 shows a graph depicted by plotting the incidence rate of the stroke on Y axis and the time after the start of the trial on X axis, and Table 2 shows the incidence rate of stroke and the inhibition rate in the EPA-E administration group at 1 to 5 years after the start of the administration.

TABLE 2

|  | Incidence rate (%) in Control group | Incidence rate (%) in EPA-E group | Inhibition Rate (%) |
|---|---|---|---|
| After 1 year | 2.0 | 2.1 | — |
| After 2 years | 3.9 | 3.6 | 8 |
| After 3 years | 5.6 | 4.7 | 16 |
| After 4 years | 8.8 | 5.7 | 35 |
| After 5 years | 11.7 | 7.4 | 37 |

As demonstrated, the incidence rate of stroke was reduced by the administration of the EPA-E, and in particular the reduction of the incidence rate of stroke was shown to be significant at 3 years or later after the start of the administration.

The numbers of cases in the control group and the EPA-E administration group were further examined for each type of stroke, and the results for cerebral thrombosis and total of infarction type diseases are shown in Table 3. Both the number of cases and the incidence rates were also lower for the hemorrhage type diseases in the EPA-E administration group.

TABLE 3

|  | Control group Stroke cases/All cases (incidence rate, %) | EPA-E group Stroke cases/All cases (incidence rate, %) |
|---|---|---|
| Cerebral thrombosis | 23/457 (5.7%) | 13/485 (2.9%) |
| Total of infarctions | 39/457 (9.5%) | 28/485 (6.20) |

Similarly, for the cases where serum TG/HDL-C ratio was known (but excluding the cases where TG value was 400 mg/dl or more), each of the three groups of subjects, which are divided based on the serum TG/HDL-C ratio at the time of registration, was analyzed on the number of onset (recurrence) of stroke, the incidence rate (%), and the odds ratio for the EPA-E group in relation to the control group during the observation period of 5 years, as shown in Table 4. The odds ratio was calculated by the equation of (incidence rate of the EPA-E group)/(incidence rate of the control group), and the inhibition rate of onset of stroke was calculated by the equation of {((incidence rate of stroke for the control group)−(incidence rate of stroke for the EPA-E group))/(incidence rate of stroke for the control group)}×100.

TABLE 4

| serum TG/HDL-C ratio | Control group Stroke cases/All cases (incidence rate, %) | EPA-E group Stroke cases/All cases (incidence rate, %) | Odds ratio |
|---|---|---|---|
| Less than 1 | 0/25 (0.0) | 0/18 (0.0) |  |
| 1 to 3.75 | 20/223 (9.0) | 14/244 (5.74) | 0.640 |
| 3.75 or more | 16/112 (14.3) | 10/135 (7.4) | 0.519 |

Figure 2:
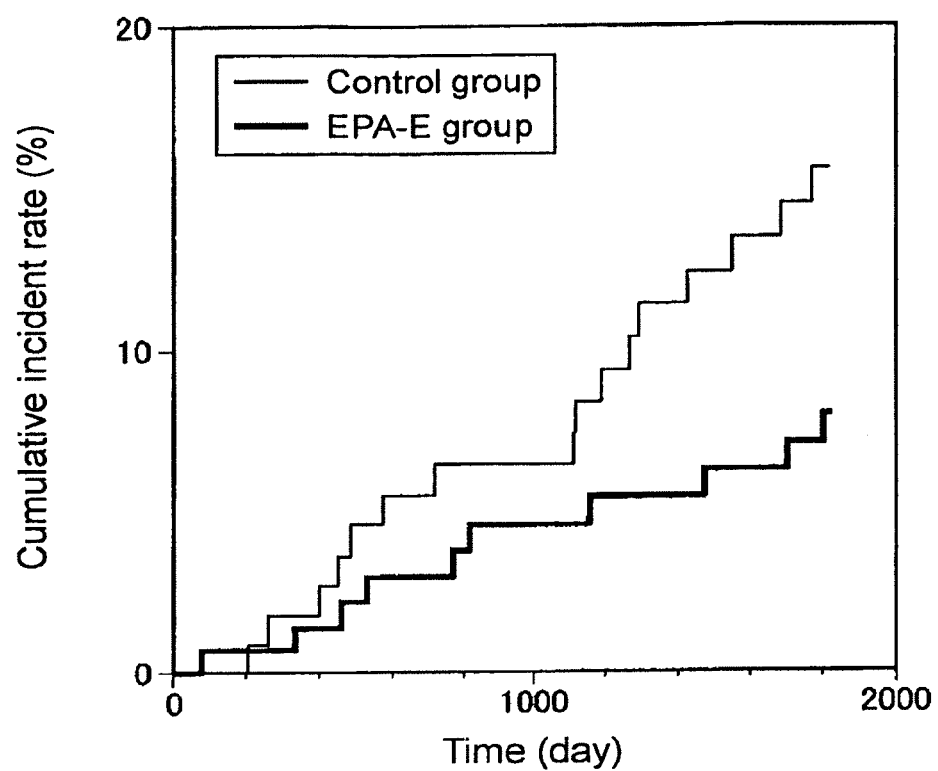
FIG. 2 is a graph prepared by plotting the incidence rate of stroke on Y axis and the time after the start of the trial on X axis, for the EPA-E group and the control group of the patients whose serum TG/HDL-C ratio at the time of registration was 3.75 or more and the serum TG value at the time of registration was less than 400 mg/dL, in an example of the present invention.

From the results in Table 4, there is shown a tendency that the higher is the serum TG/HDL-C ratio at the time of registration, the higher is the incidence rate of stroke. The administration of EPA-E reduced the incidence rate of stroke in the subjects with the history of stroke during the five year period compared to the incidence rate of the control group. That is, in the group where serum TG/HDL-C ratio was lower than 1, no onset of stroke was observed in both the control group and the EPA-E group, while in the group where the serum TG/HDL-C ratio at the time of registration was 1 or more but less than 3.75, the incidence rate of stroke in the EPA-E group was 5.74%, a lower value than the incidence rate of stroke in the control group of 9.0%, and further in the group where the serum TG/HDL-C ratio at the time of registration was 3.75 or more, the incidence rate of stroke in the EPA-E group was 7.4%, a lower value than the incidence rate of stroke in the control group of 14.3%. The odds ratio for these groups were 0.640 and 0.519, respectively, and the incidence rate of stroke was reduced by the administration of EPA-E by about 36% and about 48%, respectively, compared to the control group. Accordingly, the effect of the administration of EPA-E on preventing onset and/or recurrence of stroke was found, and the results indicate that the effect of EPA-E is higher in a group where a higher risk is predicted. Further, FIG. 2 shows a graph depicted by plotting the incidence rate of the stroke in patients whose serum TG/HDL-C ratio at the time of registration was 3.75 or more on Y axis and the time after the start of the trial on X axis, and Table 5 shows the incidence rate of stroke and the inhibition rate for the EPA-E administration group at 1 to 5 years after the start of the administration.

TABLE 5

|  | Incidence rate (%) of Control group | Incidence rate (%) of EPA-E group | Inhibition Rate (%) |
|---|---|---|---|
| After 1 year | 1.8 | 1.5 | 17 |
| After 2 years | 6.3 | 2.9 | 53 |
| After 3 years | 6.3 | 4.4 | 29 |
| After 4 years | 11.6 | 5.2 | 55 |
| After 5 years | 14.2 | 7.4 | 48 |

It was found that the incidence rate of stroke was reduced by the administration of EPA-E, and in particular the reduction of the incidence rate of stroke was shown to be significant at 3 years or later after the start of the administration. When compared with the chronological results of all the cases shown in Table 2, higher inhibition rates were observed at all the measuring points of 1 to 5 years after the start of the administration in the patients whose TG/HDL-C ratios were 3.75 or more, even though the group of these patients are predicted to have higher concentration of sdLDL, known as super-bad cholesterol, and therefore predicted to be at higher risk for onset of stroke.

From the results as described above, the significant effect of the EPA-E administration on preventing onset of stroke in patients with history of stroke was demonstrated.

INDUSTRIAL APPLICABILITY

The composition of the present invention as described above, which contains at least EPA-E as its effective component, is useful for preventing onset and/or recurrence of stroke. In particular, the composition of the present invention is expected to be effective for preventing onset and/or recurrence of stroke in hyperlipidemia patients who have been treated with HMG-CoA RI, or in particular for preventing recurrence of stroke in patients who are beyond six months after the onset of stroke. When the composition of the present invention is used in combination with HMG-CoA RI, its effect is further synergistically enhanced, and such combined use is expected to further increase the effect for preventing the onset and/or recurrence of stroke, and in particular, for preventing recurrence of stroke in patients who are beyond six months after the onset of stroke. Accordingly, such use of the present composition in combination with HMG-CoA RI is clinically favorable.

What is claimed is:

1. A method for reducing recurrence of stroke, comprising administering a composition comprising icosapentaenoic acid as an effective component thereof, orally to a patient at a dose of 0.3 g/day to 6.0 g/day in terms of the icosapentaenoic acid, wherein said patient is beyond six months after the onset of stroke in said patient.

2. The method according to claim 1, wherein serum triglyceride/high density lipoprotein-cholesterol (TG/HDL-C) ratio of the patient is 3.75 or more.

3. The method according to claim 2, wherein a 3-hydroxy-3-methylglutaryl coenzyme A reductase inhibitor is administered to the patient in combination with the composition comprising icosapentaenoic acid.

4. The method according to claim 2, wherein the administration of the composition comprising icosapentaenoic acid to the patient is continued for at least three years.

5. The method according to claim 2, wherein the composition comprising icosapentaenoic acid is administered to the patient at a proportion of 96.5% by weight or more in the total content of fatty acids.

6. The method according to claim 1, wherein the patient suffers from hyperlipidemia.

7. The method according to claim 6, wherein a 3-hydroxy-3-methylglutaryl coenzyme A reductase inhibitor is administered to the patient in combination with the composition comprising icosapentaenoic acid.

8. The method according to claim 6, wherein the administration of the composition comprising icosapentaenoic acid to the patient is continued for at least three years.

9. The method according to claim 6, wherein the composition comprising the icosapentaenoic acid is administered to the patient at a proportion of 96.5% by weight or more in the total content of fatty acids.

10. The method according to claim 3, wherein the 3-hydroxy-3-methylglutaryl coenzyme A reductase inhibitor is simultaneously administered to the patient with the composition comprising icosapentaenoic acid as a single combination drug.

11. The method according to claim 2, wherein the composition comprising icosapentaenoic acid is administered to the patient at a proportion of 40% by weight or more in the total content of fatty acids.

12. The method according to claim 2, wherein the composition further comprises ethyl ester of docosahexaenoic acid.

13. The method according to claim 12, wherein the composition further comprises an antioxidant.

14. The method according to claim 7, wherein the 3-hydroxy-3-methylglutaryl coenzyme A reductase inhibitor is simultaneously administered to the patient with the composition comprising icosapentaenoic acid as a single combination drug.

15. The method according to claim 6, wherein the composition comprising icosapentaenoic acid is administered to the patient at a proportion of 40% by weight or more in the total content of fatty acids.

16. The method according to claim 6, wherein the composition further comprises ethyl ester of docosahexaenoic acid.

17. The method according to claim 16, wherein the composition further comprises an antioxidant.

18. A method for reducing recurrence of stroke, comprising administering a composition comprising icosapentaenoic acid as an effective component thereof, orally to a patient at a dose of 0.3 g/day to 6.0 g/day in terms of the icosapentaenoic acid, wherein said patient has a history of stroke and a serum triglyceride/high density lipoprotein-cholesterol (TG/HDL-C) ratio of said patient is 3.75 or more.

\* \* \* \* \*